United States Patent [19]

Young

[11] Patent Number: 4,534,358
[45] Date of Patent: Aug. 13, 1985

[54] NUCLEAR MAGNETIC RESONANCE IMAGING APPARATUS

[75] Inventor: Ian R. Young, Sunbury-on-Thames, England

[73] Assignee: Picker International Limited, Wembley, England

[21] Appl. No.: 591,697

[22] Filed: Mar. 21, 1984

[30] Foreign Application Priority Data

Mar. 30, 1983 [GB] United Kingdom ............... 8308778

[51] Int. Cl.³ ............................................. A61B 5/05
[52] U.S. Cl. .................................... 128/653; 324/309; 324/318
[58] Field of Search .............. 128/653, 659; 324/309, 324/318, 320

[56] References Cited

U.S. PATENT DOCUMENTS

| 3,557,777 | 1/1971 | Cohen | 128/653 |
| 3,622,869 | 11/1971 | Golay | 324/320 |
| 4,122,386 | 10/1978 | Tomita et al. | 324/320 |
| 4,333,053 | 6/1982 | Harrison et al. | 324/309 |
| 4,449,097 | 5/1984 | Young et al. | 324/318 |

FOREIGN PATENT DOCUMENTS 0067933  12/1982  European Pat. Off. ............ 128/653

OTHER PUBLICATIONS

Renner-Smith, Damadian's Supermagnet—How He Hopes to Use It to Detect Cancer, Popular Science, Dec. 1977, pp. 76-79.

Primary Examiner—Kyle L. Howell
Assistant Examiner—Ruth S. Smith
Attorney, Agent, or Firm—Watts, Hoffmann, Fisher & Heinke Co.

[57] ABSTRACT

A nuclear magnetic resonance imaging apparatus for medical use wherein a patient to be examined is positioned on support means (1) in a sitting posture and the required magnets (7, 11) and RF coils (13, 15) are arranged so as to allow easy movement of the patient into and out of the apparatus.

6 Claims, 4 Drawing Figures

NUCLEAR MAGNETIC RESONANCE IMAGING APPARATUS

This invention relates to apparatus for carrying out examinations of patients by nuclear magnetic resonance (NMR) imaging.

In NMR imaging apparatus, pulses of radio frequency energy are applied to the subject in the presence of an applied magnetic field. Under the influence of the radio frequency pulses the magnetic moments of nuclei in the material of the subject are caused to precess about the direction of the applied magnetic field to give detectable radio frequency signals. By mapping the difference between the radio frequency signals produced in different parts of a selected region of the subject, e.g. a slice through the subject, an image of the selected region of the subject may be obtained.

Known forms of NMR imaging apparatus for medically examining patients normally include a large, normally air-cored, tubular magnet assembly disposed with its axis horizontal and having a sufficiently large aperture to accommodate at least part of the body of a patient lying on a couch. Coils arrangements required for application and detection of radio frequency signals are also normally incorporated in the assembly.

Such an arrangement presents considerable difficulties when a high throughput of patients is desirable, as when, for example, it is desired to use NMR imaging apparatus for routine screening purposes for example for routine screening for breast tumors.

It is an object of the present invention to provide an NMR imaging apparatus adapted for use for routine screening purposes.

According to the present invention an NMR imaging apparatus comprises: patient support means adapted to support a patient in a sitting posture; a magnet assembly including pole pieces on either side of the support means so as to apply a magnetic field directed substantially horizontally and perpendicularly to the forward looking direction of a patient seated in the support means, said pole pieces being connected by a yoke so disposed as not to impede acess to the support means from said direction; a first radio frequency coil arrangement for application of radio frequency signals to a patient in said support means comprising one coil positioned adjacent a back support part of said support means, and another coil adapted for movement between a corresponding position in front of a patient in the support means and a position removed therefrom to allow access to the support means from said direction; and a second radio frequency coil arrangement for detection of radio frequency NMR signals produced in a patient in the support means and adapted for mounting adjacent the part of a patient to be imaged.

Preferably said second radio frequency coil arrangement is adapted to be mounted on the patient before the patient sits on said support means.

One apparatus in accordance with the invention will now be described by way of example with reference to the accompanying drawings in which.

Figure 1:
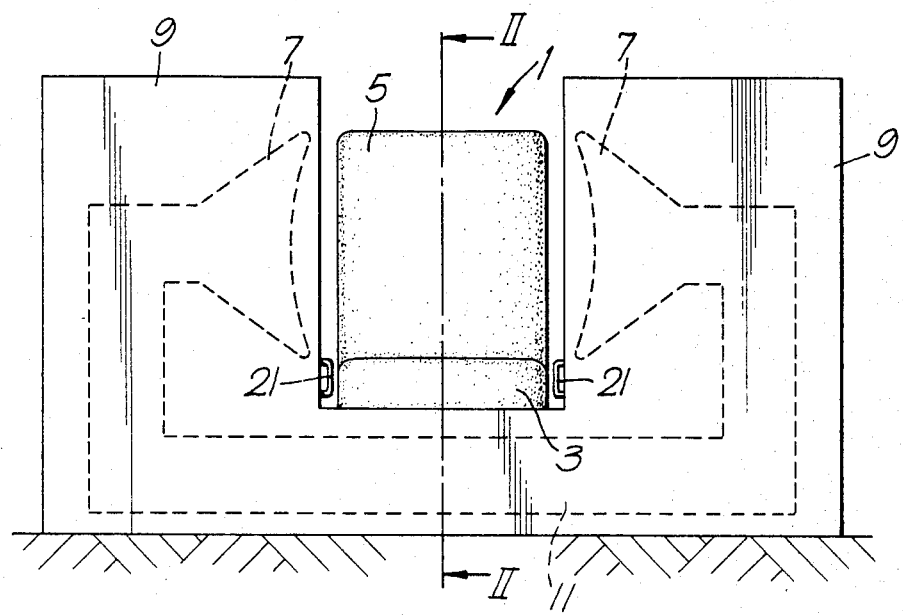
FIG. 1 is a diagrammatic front view of the apparatus, ready to receive a patient.

Referring to the drawings, the apparatus includes a support means 1 for a patient being examined having a seat portion 3 and a back portion 5 so as to support the patient in a backwardly inclined sitting position.

The support 1 is positioned between the pole pieces 7 of a magnet housed in a casing 9 having an iron yoke 11 extending between the pole pieces 7 under the seat portion 3 of the support 1, the pole pieces lying on the left and right sides respectively of a patient sitting on the support. The magnet thus provides a field extending horizontally through the torso of the patient in a direction perpendicular to the forward looking direction of the patient.

The magnet may be a permanent magnet or an electromagnetic, but in either case will be associated with coils (not shown) to enable gradients to be imposed on the field in the field direction, hereinafter referred to as the z direction, and additionally or alternatively two directions perpendicular to the field direction and respectively substantially perpendicular (x direction) and parallel (y direction) to the plane of the back portion 5 of the support 1.

Figure 2:
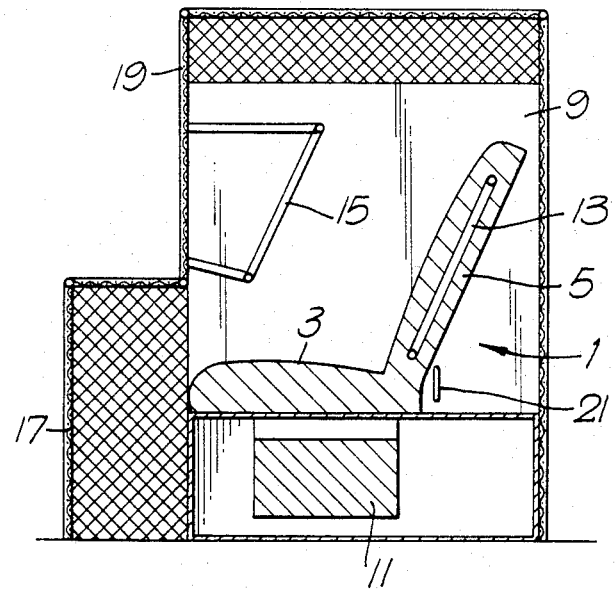
FIG. 2 is a diagrammatic sectional view along the line II—II in FIG. 1 of the apparatus in use.
Figure 3:
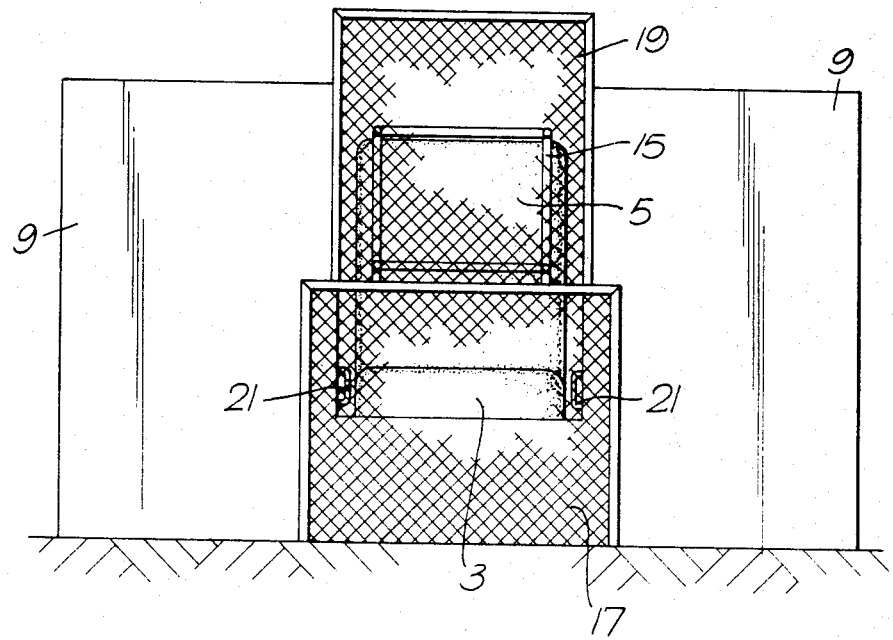
FIG. 3 is a diagrammatic front view of the apparatus in use.

The radio frequency field required for imaging is produced between two coils 13 and 15. One of its coils 13 is positioned in the back portion 5 of the support 1. The other coil 15 is positioned in operation in front of the patient, i.e. spaced from the coil 13 along the x direction. To facilitate access to the support by the patient the coil 15 is removed when imaging is not in progress. To this end a coil 15 supported on a wire mesh cage 17, 19 which is placed around the patient during imaging as shown in FIGS. 2 and 3. The cage 17, 19' serves as a radio frequency screen to confine the RF fields used during imaging to the region of the patient, and to prevent interference from external fields before and after imaging the cage 17, 19 together with coil 15 is removed, as shown in FIG. 1, to give the patient completely unobstructed access to the support 1. The cage is suitably comprised of a lower section 17 fitting around the legs of the patient and an upper section 19 from which the coil 15 is supported. The mesh of the cage is made sufficiently open for the patient to look through the cage with little obstruction, thus avoiding any claustrophobic feelings by the patient.

To facilitate imaging handles, such as 21 in the drawings, may be provided which the patient grips during imaging to suitably orientate the part of the anatomy to be imaged.

Figure 4:
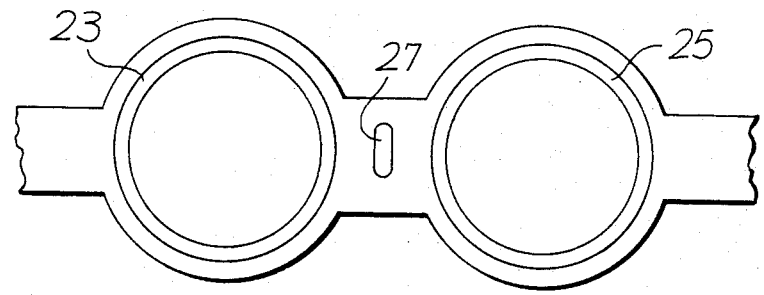
FIG. 4 shows diagrammatically a coil arrangement used in the apparatus.

Detection of radio frequency signals is obtained by coils fitted to the part of the patient's anatomy it is desired to image. Referring to FIG. 4, for breast screening two sets of coils 23 and 25 may be formed into a brassiere arrangement, thus providing two independent detectors. Various sizes of these are made available in an ante-room, and while one patient is being imaged, the next patient is fitted with an appropriately sized detector coil arrangement by a technician. A facility for testing fitted coils, e.g. a Q meter, may be provided in the ante-room.

A similar concept may be employed for imaging other parts of the anatomy e.g. for examination in respect of spinal disorders.

Where two independent detectors are used, the NMR imaging apparatus may be arranged to process the signals produced by the two detectors simultaneously in separate channels, thereby halving imaging time.

The imaging sequence used will of course depend on the part of the anatomy being imaged and the purpose of the examination.

For breast screening a suitable sequence is a multi-slice two dimensional Fourier transform spin echo sequence. Typically, for a breast scan, the slices will be in the x-y plane, with the slices of thickness and spacing 2 millimeters and a maximum of 8 slices per detector taken at a time. Thus two passes will cover a 32 millimeter thick region in sixteen slices.

Options in respect of slice thickness and spacing and orientation will normally be provided for other work. Also, whilst breast screening will normally be done using the above described spin echo sequence, a standard inversion recovery sequence will normally also be available so that a suspect can be verified using another technique. A fast repeated FID sequence is suitably provided for spinal definition and to facilitate extraction of $T_1$ (spin lattice relaxation time) and $T_2$ (spin-spin relaxation time) values.

It will be understood that for satisfactory imaging the location of the detector coils in the data recovery magnetic field gradient must be taken account of. To this end each detector coil set is associated with an NMR probe, for example, a small doped water cell as shown at 27 in FIG. 4. At suitable intervals during each scanning procedure the normal sequence is interrupted and data extracted from the probe or probes through the channel or channels normally used for data recovery. The resulting signals are used to locate the coil positions and define appropriate frequencies for use in recovering image data.

For example, if the machine control frequency i.e. the expected frequency of signals obtained from material in a median plane through the machine is fo, and the frequency of the signal obtained from a probe by demodulating its output using a signal of frequency fo is df1, then from a knowledge of the applied gradient field G and the gyromagnetic ratio $\gamma$ of the probe material, the displacement x of the probe from the median plane is given by $$x = \frac{df1}{\gamma G}$$

From a knowledge of the detector coil dimensions and the position of the probe in relation to the center of the coil, the center frequency for the coil in the data recovery gradient can then be determined, and this frequency used to demodulate the image data.

I claim:

1. A nuclear magnetic resonance imaging apparatus comprising: patient support means adapted to support a patient in a sitting posture; a magnet assembly means including two pole pieces, one on each side of the support means so as to apply a magnetic field directed substantially horizontally and perpendicularly to the forward looking direction of a patient seated in the support means, said pole pieces being connected by a yoke so disposed as not to impede access to the support means from said direction; a first radio frequency coil means for application of radio frequency signals to a patient in said support means comprising one coil means positioned adjacent a back support part of said support means, and another coil means adapted for movement between a corresponding position in front of a patient in the support means and a position removed therefrom to allow access to the support means from said direction; and a second radio frequency coil means for detection of radio frequency NMR signals produced in a patient in the support means and adapted for mounting adjacent the part of a patient to be imaged.

2. An apparatus according to claim 1 wherein said yoke extends beneath said support means.

3. An apparatus according to claim 1 including a radio frequency screen means adapted to be positioned around a patient in the support means in use of the apparatus, said another coil means being mounted on said screen means.

4. An apparatus according to claim 1 wherein said second radio frequency coil means includes means for mounting said second coil means on a patient before the patient sits on said support means.

5. An apparatus according to claim 4 wherein said second coil arrangement carries a probe means arranged to produce an output signal including means for locating the position of said second coil arrangement with respect to the applied magnetic field.

6. An apparatus according to claim 1 wherein said second radio frequency coil means includes at least two coils each comprising means for detecting independently NMR signals produced in a different part of a patient.

* * * * *